(12) United States Patent
Cha et al.

(10) Patent No.: US 7,690,284 B2
(45) Date of Patent: Apr. 6, 2010

(54) SAFE LANCET DISPOSER

(76) Inventors: Eun Jong Cha, Jukong Apt. 208-205, Mochung-Dong, Heungdeok-Gu, Cheongju-City, Chungcheongbuk-Do 361-753 (KR); Mi Sook Park, 201-401, Hyundai 2 Apt., Yongam-Dong, Sangdang-Gu, Cheongju-City, Chungcheonbuk-Do (KR) 360-161; Kyung Ah Kim, 1207, Duk Apt., Sajik 2-Dong, Heungdeok-Gu, Cheongju-City, Chungcheonbuk-Do (KR) 361-753

( * ) Notice: Subject to any disclaimer, the term of this patent is extended or adjusted under 35 U.S.C. 154(b) by 632 days.

(21) Appl. No.: 10/562,700

(22) PCT Filed: Apr. 26, 2004

(86) PCT No.: PCT/KR2004/000958

§ 371 (c)(1),
(2), (4) Date: Sep. 5, 2006

(87) PCT Pub. No.: WO2005/102167

PCT Pub. Date: Nov. 3, 2005

(65) Prior Publication Data

US 2007/0102312 A1    May 10, 2007

(30) Foreign Application Priority Data

Apr. 23, 2004   (KR) .................... 10-2004-0028053

(51) Int. Cl.
   *B26D 7/00*   (2006.01)
(52) U.S. Cl. ............... 83/167; 83/944; 30/131; 30/241; 30/242
(58) Field of Classification Search ............ 83/167, 83/944; 30/131, 242, 241, 124, 125, 134; 604/110; 206/364–366
   See application file for complete search history.

(56) References Cited

U.S. PATENT DOCUMENTS

| 3,736,824 A | * | 6/1973 | Dunnican et al. | 83/167 |
| 3,914,865 A | * | 10/1975 | Oakes | 30/131 |
| 4,035,911 A | * | 7/1977 | Nethercutt et al. | 30/131 |
| 4,255,996 A | * | 3/1981 | Choksi et al. | 83/140 |
| 4,275,628 A | * | 6/1981 | Greenhouse | 83/167 |
| 4,315,448 A | * | 2/1982 | Ball | 83/167 |
| 4,404,881 A | * | 9/1983 | Hanifl | 83/167 |
| 4,417,460 A | * | 11/1983 | Moriconi | 72/325 |
| 4,565,311 A | * | 1/1986 | Pugliese et al. | 225/94 |
| 4,614,035 A | * | 9/1986 | Andrews | 30/124 |

(Continued)

*Primary Examiner*—Boyer D Ashley
*Assistant Examiner*—Omar Flores-Sánchez
(74) *Attorney, Agent, or Firm*—Birch, Stewart, Kolasch & Birch, LLP

(57) ABSTRACT

The object of this invention is to provide a safe lancet disposer which prevents a lancet, having been used for blood collection, from being reused, thus preventing secondary infection and cross infection. The safe lancet disposer (100) of the present invention includes a cutting unit (110) which cuts an end of a needle of a lancet, a receiving unit (140) which is disposed under the cutting unit (110) to receive therein the cut end of the needle, and an operating unit (170) which is rotatably mounted to the receiving unit (140) and operates the cutting unit (110). The cutting unit (110) has an insertion plate (112), a support plate (118) and a cutting plate (128). The receiving unit (140) has a receiving housing (142) and a receiving container (160). The operating unit (170) has an operating lever (172).

7 Claims, 7 Drawing Sheets

U.S. PATENT DOCUMENTS

| | | | | |
|---|---|---|---|---|
| 4,867,309 A | * | 9/1989 | Germain | 206/366 |
| 4,969,379 A | * | 11/1990 | Taylor et al. | 83/167 |
| 5,187,850 A | * | 2/1993 | McCammon et al. | 29/235 |
| 5,340,039 A | * | 8/1994 | Lefevre | 241/84 |
| 5,467,930 A | * | 11/1995 | Lefevre | 241/84 |
| 6,545,242 B1 | * | 4/2003 | Butler | 219/68 |
| 6,575,992 B1 | | 6/2003 | Takakura | |
| 7,389,873 B2 | * | 6/2008 | Johnson aka Mindes | 206/366 |

\* cited by examiner

SAFE LANCET DISPOSER

TECHNICAL FIELD

The present invention relates, in general, to safe lancet disposers and, more particularly, to a safe lancet disposer which includes a cutting unit that cuts an end of a needle of a lancet used in blood collection, a receiving unit which is disposed under the cutting unit to receive therein the cut end of the needle, and an operating unit which is rotatably mounted to the receiving unit and operates the cutting unit, thus preventing the lancet, which was used for the blood collection, from being reused, thereby preventing secondary infection and cross infection, and safely storing and discarding the cut needle.

BACKGROUND ART

Generally, chronic diabetics must conduct blood glucose tests at home every day to maintain the blood glucose at a constant level. To conduct such a blood glucose test, the blood of a diabetic must be collected. To collect the blood, typically, the diabetic pricks a location on his/her body, for example, a finger, with a disposable lancet and, thereafter, smears collected blood on a strip. The strip is mounted to a blood glucose testing machine so as to measure a blood glucose level.

As such, lancing devices have been widely used as devices for collecting blood. Such a lancing device includes a lancet holder, to which a disposable lancet is mounted, an end cap, which covers the lancet and has a hole such that only the end of a needle is allowed to pass through the hole when pricking the skin of the diabetic, and a spring and a percussion device, which generate a skin penetration force. To use the lancing device, first, the end cap is removed from the lancing device. Thereafter, the lancet is coupled to the lancet holder while the spring is contracted. In a state such that the spring is compressed, the end cap is again coupled to the lancing device. After the end cap is brought into close contact with a location of a user at which many capillaries exist, the lancet is actuated by manipulating a percussion switch. Then, the needle pricks the skin of the user. Thereafter, the user squeezes the area around the pricked portion to obtain sufficient blood. Subsequently, the user smears the blood on the strip and measures the blood glucose. In this process, because the needle of the lancet enters the skin of the user and is removed, the end of the needle of the lancet is smeared with blood of the user. If this lancet is not removed from the lancing device, the user may be exposed to a secondary infection. As well, if another person carelessly uses this lancet, cross infection may occur. Particularly, in the case of a contagious disease such as AIDS, a fatal result may be caused.

However, to date, there is no method of safely scrapping a lancet after a patient has used the lancet for blood collection. Because most lancets used in blood collection are scrapped along with general garbage, there is a possibility of infection. Moreover, there is a problem in that, when a person handles waste including lancets used in blood collection therein, the person may be pricked by the lancet, thus becoming infected.

DISCLOSURE OF THE INVENTION

Accordingly, the present invention has been made keeping in mind the above problems occurring in the prior art, and an object of the present invention is to provide a safe lancet disposer which includes a cutting unit that cuts the end of a needle of a lancet used in blood collection, a receiving unit which is disposed under the cutting unit to receive therein the cut end of the needle, and an operating unit which is rotatably mounted to the receiving unit and operates the cutting unit, thus preventing the lancet, having been used for blood collection, from being reused, thereby preventing secondary infection and cross infection, and safely storing and scrapping the cut needle.

BEST MODE FOR CARRYING OUT THE INVENTION

In order to accomplish the above object, the present invention provides a safe lancet disposer, including:

a cutting unit, having: an insertion plate having therein an insertion hole into which an end of a needle of a lancet used for blood collection is inserted; a support plate disposed under the insertion plate, with a guide groove formed in an upper surface of the support plate and extending from a first end of the support plate towards a second end, an elongated guide hole formed in the guide groove and communicating with the insertion hole, and a guide slot extending from the second end of the support plate to an intermediate position along the guide groove; and a cutting plate movably disposed in both the guide groove and the guide slot, with a cutting hole formed in the cutting plate and communicating with both the insertion hole and the elongated guide hole so as to cut the end of the needle inserted into the cutting hole through the insertion hole, a stop protrusion integrally provided under the cutting plate and extending towards the guide slot, and a mounting hole formed through the cutting plate;

a receiving unit, having: a receiving housing perpendicularly disposed under the support plate, with a receiving hole longitudinally formed through the receiving housing and communicating with the elongated guide hole; and a receiving container removably inserted into the receiving hole so that the cut end of the needle which drops through the elongated guide hole is contained in the receiving container; and an operating unit, having: an operating lever rotatably mounted to a second surface of the receiving housing such that an upper end of the operating lever is coupled to the cutting plate through the guide slot, thus moving the cutting plate so as to cut the end of the needle inserted into the cutting hole.

As described above, in the present invention, the safe lancet disposer includes a cutting unit that cuts the end of a needle of a lancet used in blood collection, a receiving unit which is disposed under the cutting unit to receive therein the cut end of the needle, and an operating unit which is rotatably mounted to the receiving unit and operates the cutting unit, so that the present invention prevents the lancet, having been used for blood collection, from being reused, thereby preventing secondary infection and cross infection, and safely storing and scrapping the cut needle.

Hereinafter, a safe lancet disposer according to a preferred embodiment of the present invention will be described in detail with reference to the attached drawings.

Figure 1:
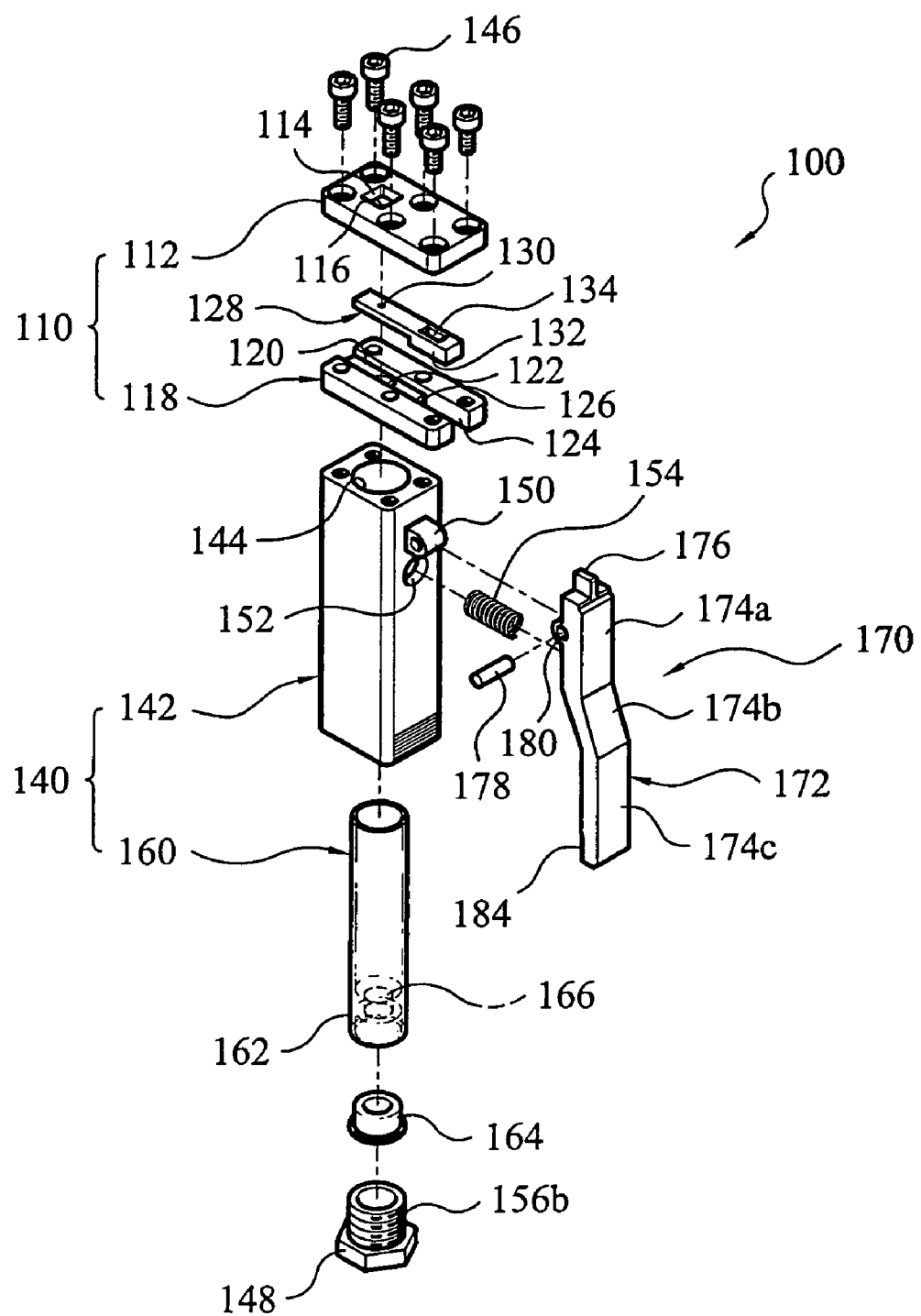
FIG. 1 is an exploded perspective view of a safe lancet disposer, according to the present invention.
Figure 2:
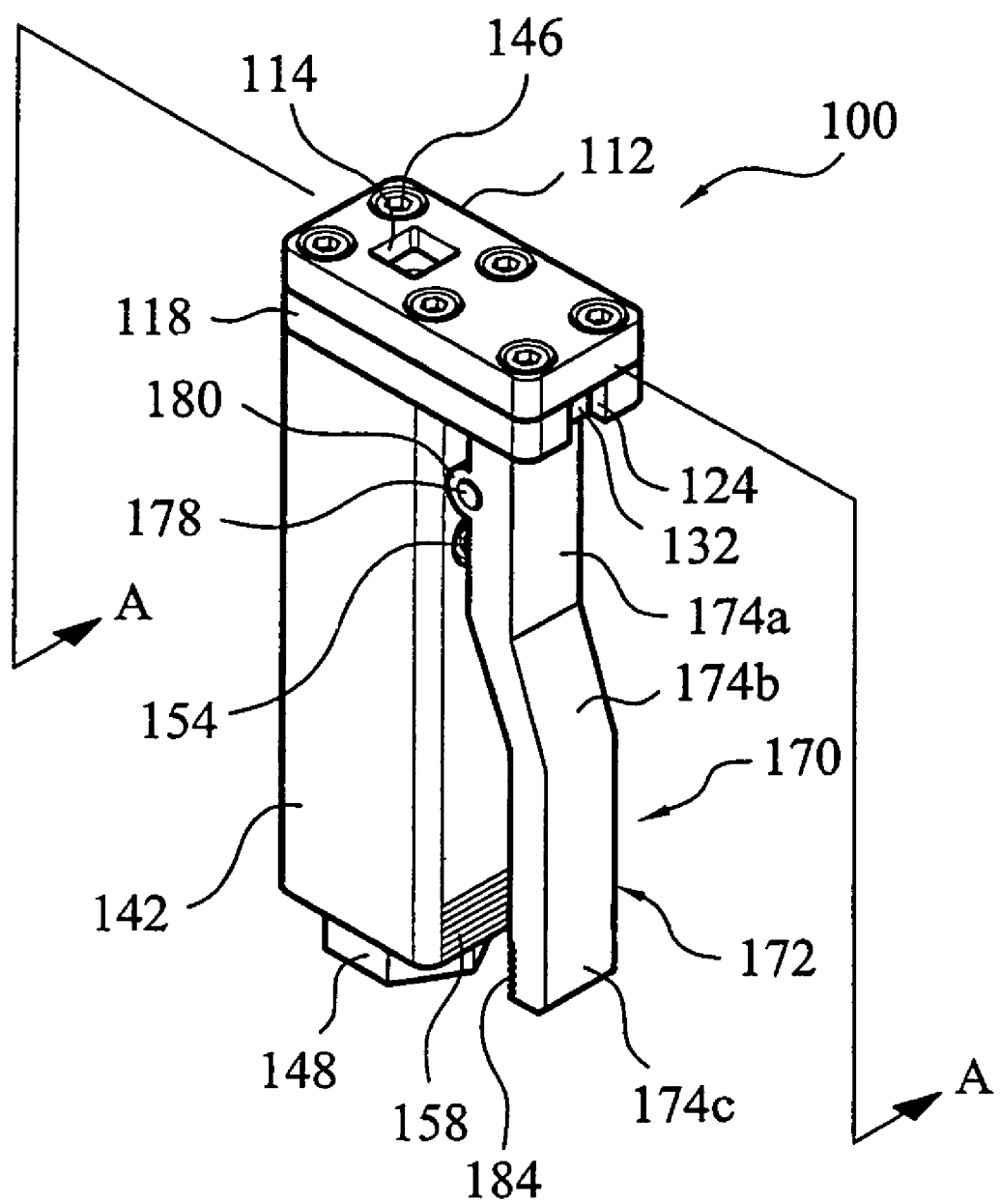
FIG. 2 is a perspective view of the assembled safe lancet disposer of FIG. 1.
Figure 3:
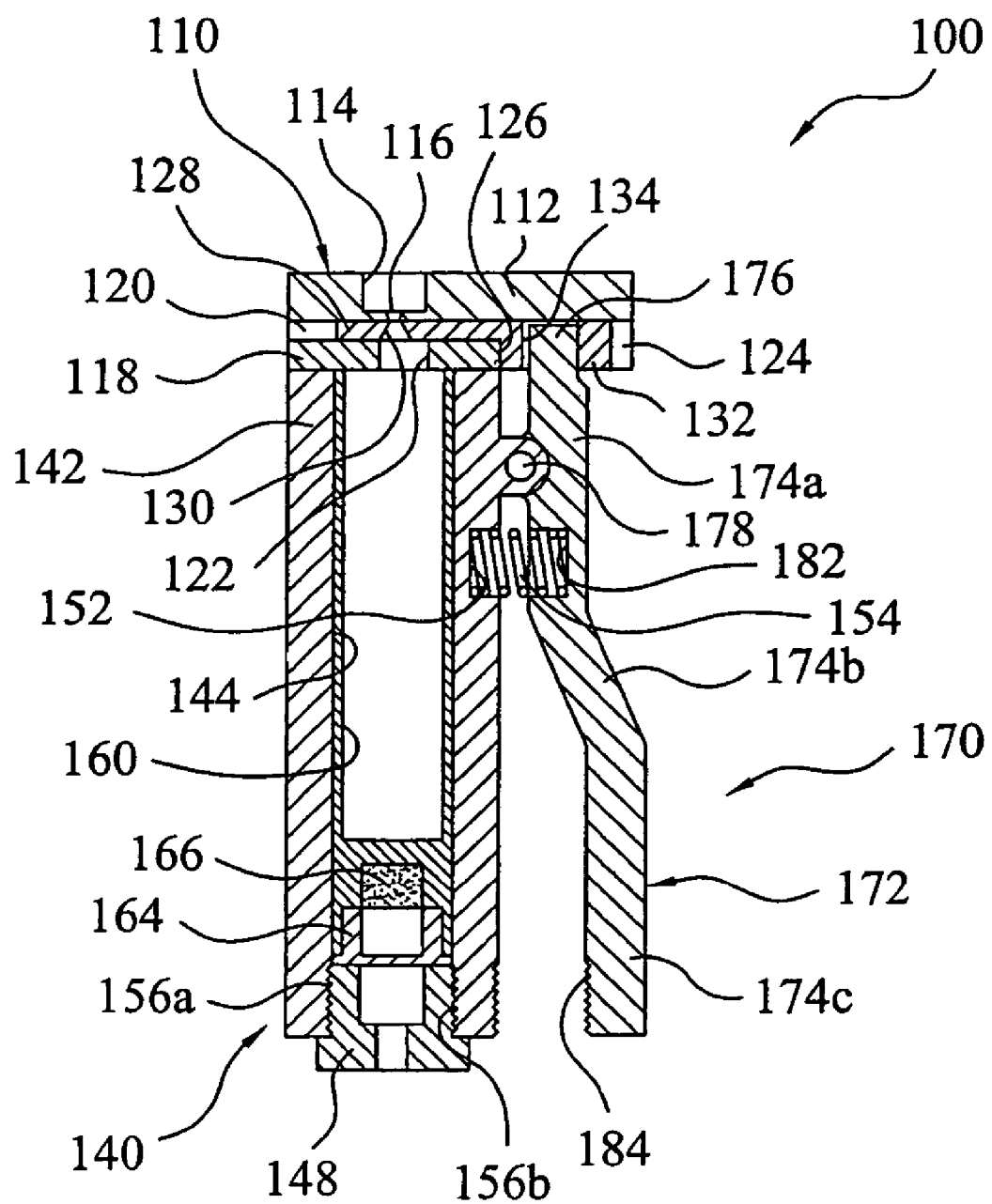
FIG. 3 is a sectional view taken along the line A-A of FIG. 2.

FIG. 1 is an exploded perspective view of the safe lancet disposer, according to the present invention. FIG. 2 is a perspective view of the assembled safe lancet disposer of FIG. 1. FIG. 3 is a sectional view taken along the line A-A of FIG. 2.

Referring to FIGS. 1 through 3, the safe lancet disposer 100 of the present invention includes a cutting unit 110 which cuts a needle (N) of a lancet (L) used in blood collection, a receiving unit 140 which is disposed under the cutting unit 110 to receive therein the cut end of the needle (N), and an operating unit 170 which is rotatably mounted to the receiving unit 140 and operates the cutting unit 110.

The cutting unit 110 includes an insertion plate 112, a support plate 118 and a cutting plate 128. The insertion plate 112 has a planar plate shape. An insertion groove 114 is provided in an upper surface of the insertion plate 112 so that an end of the lancet (L) is brought into close contact with a bottom of the insertion groove 114. An insertion hole 116 is formed through the insertion plate 112 in the insertion groove 114, so that an end of the needle (N) protruding from the end of the lancet (L) to be used for blood collection is inserted into the insertion hole 116. The support plate 118 is disposed under the lower surface of the insertion plate 112. A guide groove 120 is formed in an upper surface of the support plate 118 and extends from a first end of the support plate 118 towards a second end. An elongated guide hole 122 is formed in the guide groove 120 and communicates with the insertion hole 116. A guide slot 124 extends from the second end of the support plate 118 to an intermediate position along the guide groove 120 and divides the second end of the support plate 118 into two opposite parts. The cutting plate 128 is movably disposed in the guide groove 120 and the guide slot 124. A cutting hole 130, which communicates with the insertion hole 116 and the elongated guide hole 122, is formed in the cutting plate 128 to cut the end of the needle (N) when inserted into the cutting hole 130 through the insertion hole 116 and to guide the cut needle end to the elongated guide hole 122. A stop protrusion 132, a surface of which is in close contact with a stop surface 126, is integrally provided under the cutting plate 128 which extends towards the guide slot 124. A mounting hole 134 is formed through the stop protrusion 132 of the cutting plate 128. Preferably, the insertion hole 116 has a shape which is reduced in diameter from the top to the bottom. Furthermore, it is preferable that the cutting hole 124 have a shape which is enlarged in diameter from the top of the guide groove 120 to the bottom. The receiving unit 140 is mounted to the cutting unit 110 having the above-mentioned construction.

The receiving unit 140 includes a receiving housing 142 and a receiving container 160. The receiving housing 142 is perpendicularly disposed at a predetermined position under the lower surface of the support plate 118. A receiving hole 114, which communicates with the elongated guide hole 122, is longitudinally formed through the receiving housing 142. The receiving housing 142 is coupled to the support plate 118 and the insertion plate 112 by a plurality of locking bolts, which are tightened into the receiving housing 142 after passing through the support plate 118 from the upper surface of the insertion plate 112. A lower surface of the receiving housing 142 is defined by a stopper 148 which openably closes the receiving hole 144. A first hinge protrusion 150 is provided on a second surface of the receiving housing 142 at a position adjacent to an upper end of the receiving housing 142. A first spring seat 152 is formed in the second surface of the receiving housing 142 below the first hinge protrusion 150, so that a first end of a lever spring 154 is inserted into the first spring seat 152. Preferably, an internal thread 156a is formed on a lower end of an inner surface of the receiving hole 144, and an external thread 156b is formed on a circumferential outer surface of the stopper 148, so that the external thread 156b engages with the internal thread 156a. Moreover, it is preferred that a first knurled surface 158 be formed at a lower position on the second surface of the receiving housing 142. The receiving container 160 has a cylindrical shape which is opened at an upper end thereof and closed at a lower end thereof such that the cut end of the needle (N) which drops through the elongated guide hole 122 is contained in the receiving container 160. Furthermore, the receiving container 160 is removably inserted into the receiving hole 144. A lid holding ring 162 integrally extends downwards from the lower end of the receiving container 160, and a lid 164 is held by the lid holding ring 162, so that, when it is desired to discard the receiving container 160 after the receiving container 160 becomes filled with cut ends of needles (N), the open upper end of the receiving container 160 is closed using the lid 164. Preferably, a magnet 166 is installed in the lower end of the receiving container 160, so that the cut ends of the needles (N) are held by the magnet 166 in the receiving container 160. The operating unit 170 is mounted to the receiving unit 140 having the above-mentioned construction.

The operating unit 170 includes an operating lever 172 which is mounted to the second surface of the receiving housing 142. The operating lever 172 includes a first lever body 174a which extends downwards from a position level with the upper end of the second surface of the receiving housing 142, a second lever body 174b which extends from a lower end of the first lever body 174a outwards and downwards at a predetermined angle with respect to the second surface of the receiving housing 142, and a third lever body 174c which extends downwards from a lower end of the second lever body 174b. Furthermore, an operating protrusion 176 is integrally provided on an upper surface of the first lever body 174a and is inserted into the mounting hole 134 formed in the stop protrusion 132. Second hinge protrusions 180 are provided on a first surface of the first lever body 174a so that the second hinge protrusions 180 are rotatably mounted to the first hinge protrusion 150 via a hinge 178 while being in close contact with opposite sides of the first hinge protrusion 150. A second spring seat 182 is formed in the first lever body 174a below the second hinge protrusions 180 so that a second end of the lever spring 154, which extends outside from the first spring seat 152, is inserted into the second spring seat 182. Preferably, a second knurled surface 184 is formed on a lower end of the third lever body 174c at a position facing the first knurled surface 158.

The operation of the safe lancet disposer 100 having the above-mentioned construction will be explained in brief herein below.

To conduct a blood glucose test, a user removes an end cap (E) from a lancing device (D) and mounts a lancet (L) to a lancet holder (not shown). Subsequently, the user again mounts the end cap (E) on the lancing device (D) and then measures a blood glucose level with the lancing device (D). Thereafter, a needle (N) of the lancet (L), which was used for measuring the blood glucose level, is cut.

Figure 4A:
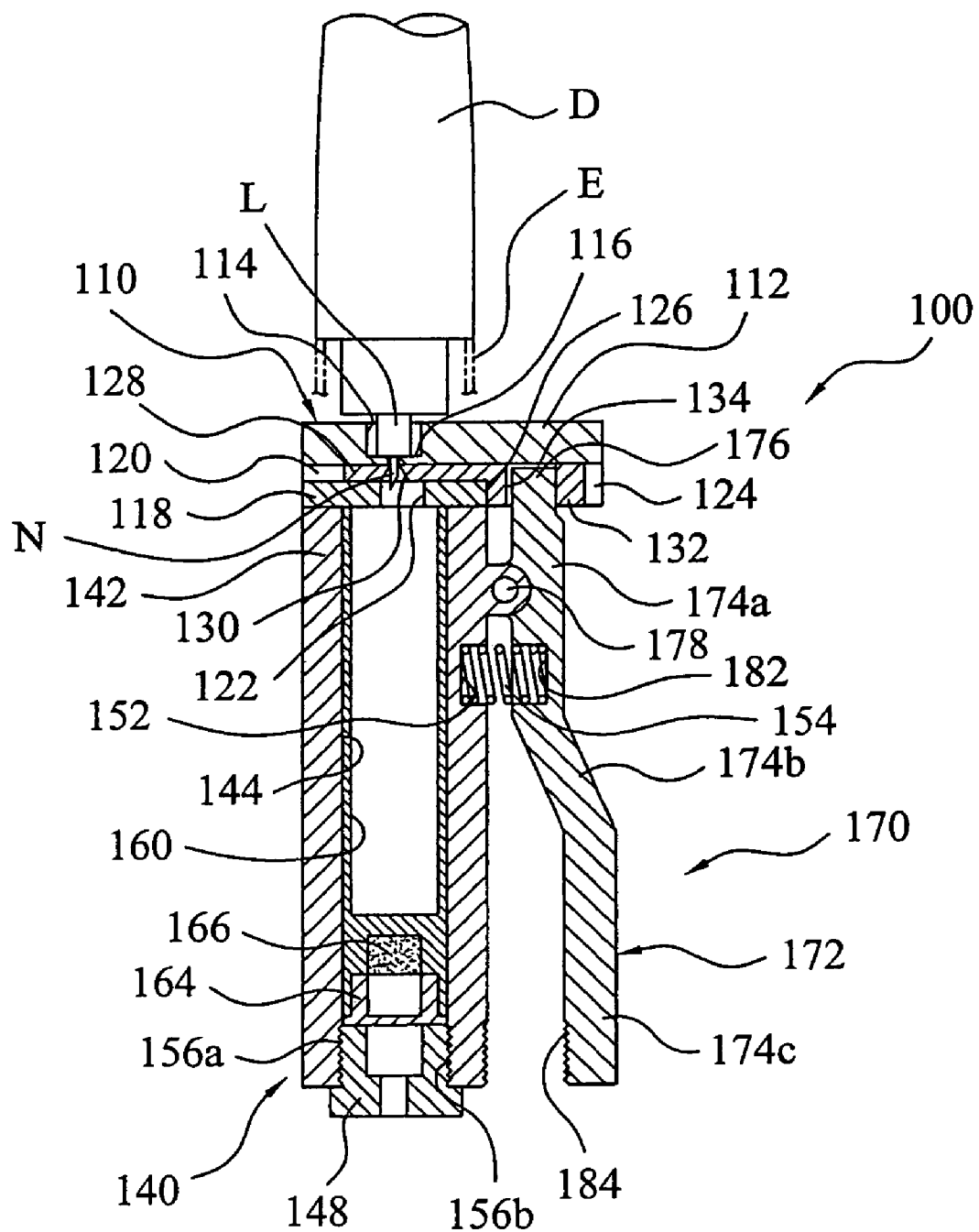
FIGS. 4a and 4b are sectional views showing a method of cutting an end of a needle of a lancet using the safe lancet disposer according to the present invention.
Figure 4B:
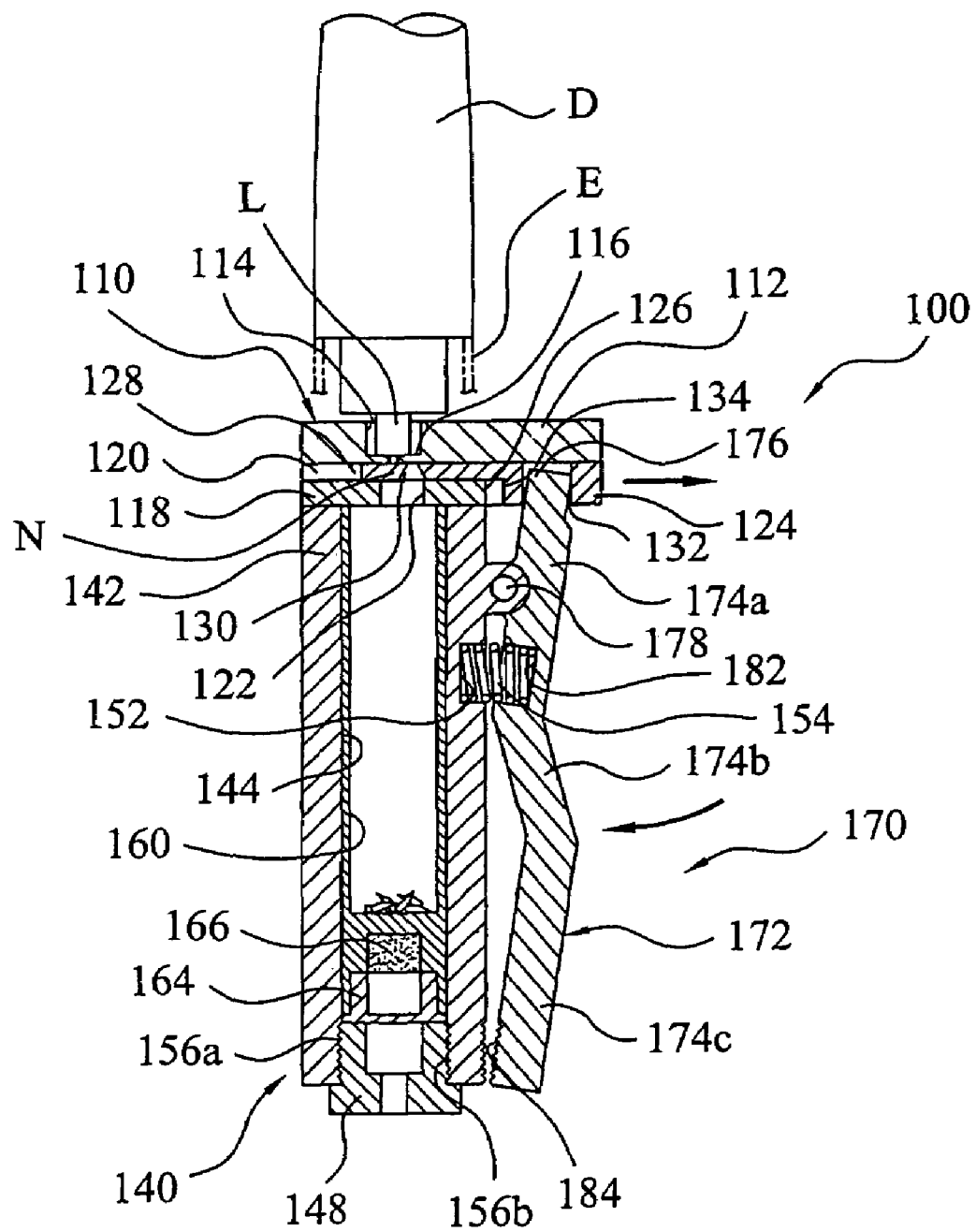

FIGS. 4a and 4b are sectional views showing a method of cutting an end of the needle of the lancet using the safe lancet disposer of the present invention.

Referring to FIGS. 4a and 4b, the user holds the lancing device (D), from which the end cap (E) has been removed, with one hand and inserts the lancet (L), with which blood is smeared, into the insertion groove 114 such that the end of the needle (N), which protrudes from the lancet (L), is inserted into the insertion hole 116. Then, the end of the needle (N), which is inserted in the insertion hole 116, is positioned in the elongated guide hole 112 through the cutting hole 130.

As such, when the end of the needle (N) is in the insertion hole 116, the cutting hole 130 and the elongated guide hole 122, the user pushes the operating unit 170 towards the receiving unit 140 while holding the receiving unit 140 and the operating unit 170 with one hand. Then, the operating lever 172 rotates towards the receiving housing 142 around the first and second hinge protrusions 150 and 180, which are coupled to each other by the hinge 178. As the operating lever 172 rotates, the lever spring 154 contracts and the operating protrusion 176 of the first lever body 174a of the operating lever 172 moves the cutting plate 128, along with the stop protrusion 132, towards the second end of the support plate 118 along the guide groove 120. As a result, the end of the needle (N) of the lancet (L), which is in the cutting hole 130, is cut between the moving cutting hole 130 and the stationary insertion hole 114. Then, the cut end of the needle (N) drops into the receiving container 160, which is provided in the receiving hole 44 of the receiving housing 142, after passing through the elongated guide hole 122. The dropped end of the needle (N) is stably contained in the receiving container 160 without moving by the magnet 166, which is installed in the lower end of the receiving container 160.

As such, after the needle (N) of the lancet (L) is cut, the operating unit 170, which has been pushed towards the receiving unit 140, is released. Then, the lever spring 154, which was contracted, returns to its initial state, thus restoring the operating lever 172. While the operating lever 172 is returned to its initial state, the operating protrusion 176 moves the stop protrusion 132 and the cutting plate 128 until a surface of the stop protrusion 132 comes into contact with the stop surface 126. Then, the insertion hole 116, the cutting hole 130 and the elongated guide hole 122 again communicate together.

Figure 5A:
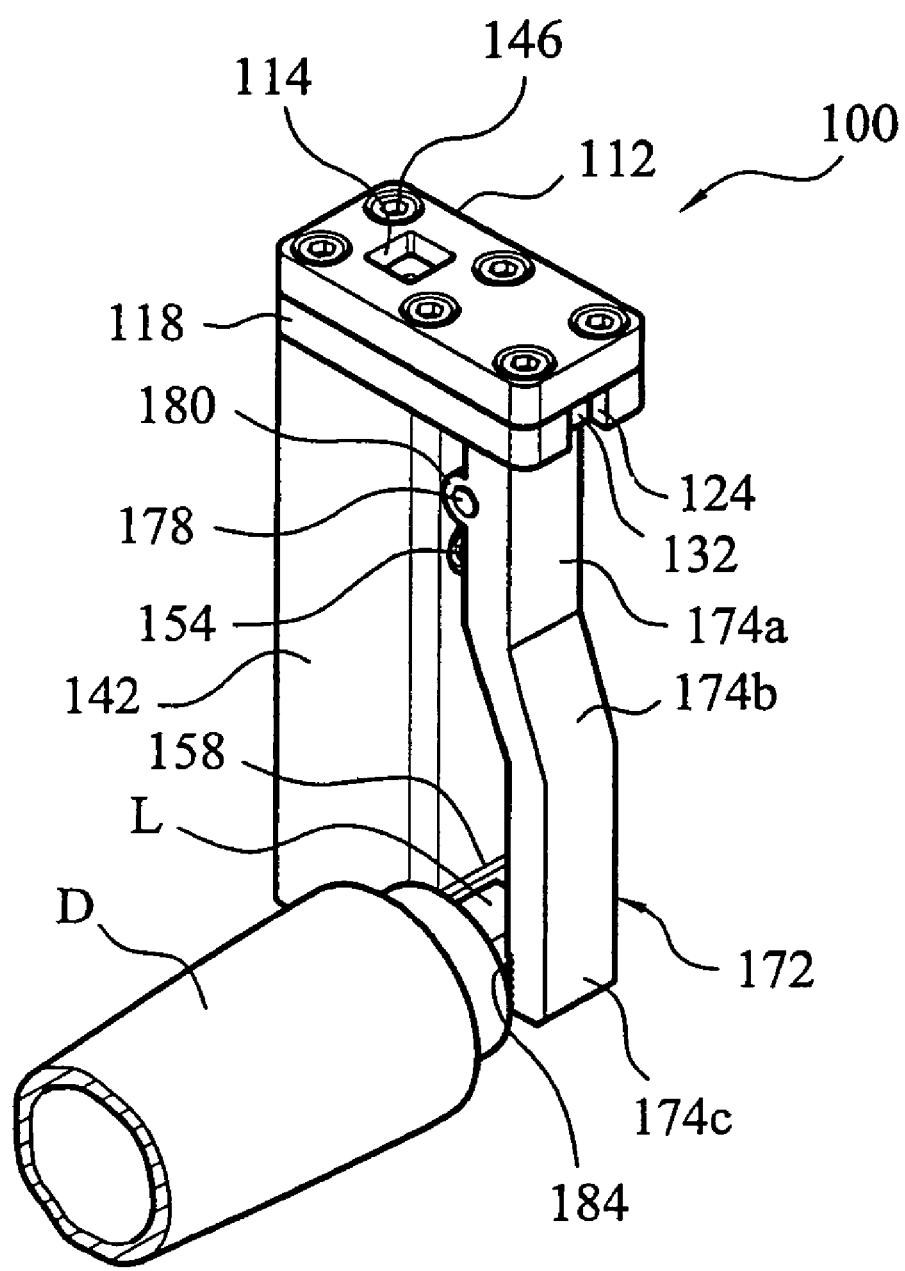
FIGS. 5a and 5b are perspective views showing a method of removing the lancet, the needle of which has been cut, from a lancing device using the safe lancet disposer according to the present invention.
Figure 5B:
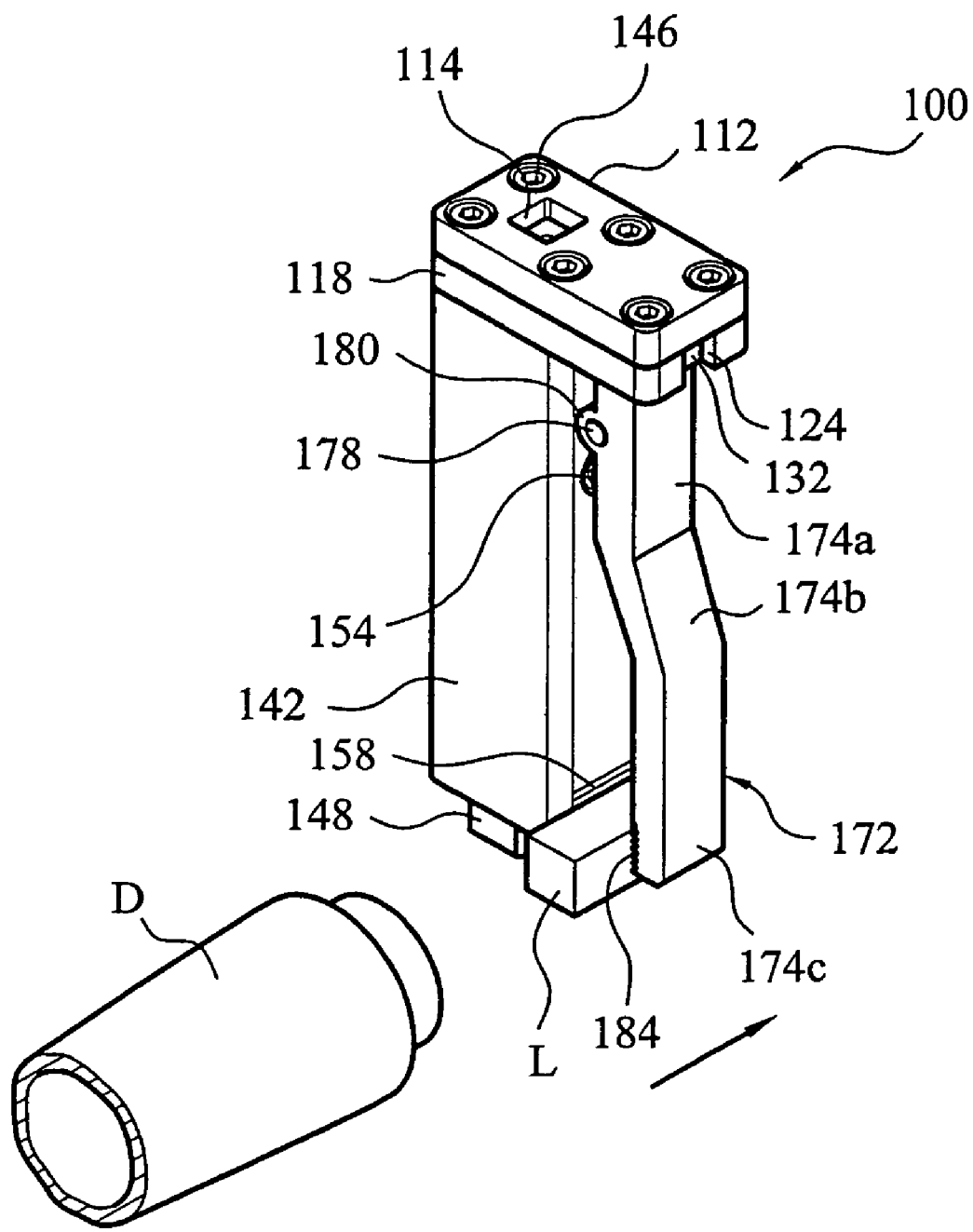

FIGS. 5a and 5b are perspective views showing a method of removing the lancet, the needle of which has been cut, from the lancing device using the safe lancet disposer according to the present invention. Referring to FIGS. 5a and 5b, to remove the lancet (L), the needle (N) of which has been cut, from the lancet holder of the lancing device (D), in a state in which the safe lancet disposer 100 is turned upside down or the lancing device (D) is oriented sideways, the lancet (L), which protrudes from the lancing device (D), is disposed between the first and second knurled surfaces 158 and 184. Thereafter, the operating lever 172 is pressed, so that the third lever body 174c of the operating lever 172 rotates towards the receiving housing 142, thus holding the lancet (L). As such, after the lancet (L) is held between the first and second knurled surfaces 158 and 184, the user pulls the safe lancet disposer 100 or the lancing device (D) to remove the lancet (L) from the lancing device (D), and then discards the lancet (L).

Meanwhile, when the number of cut ends of needles (N), which have been collected in the receiving container 160, reaches a desired level, the user opens the stopper 148, which closes the lower end of the receiving hole 144 of the receiving housing 142, and then removes the receiving container 160 from the receiving housing 142. Thereafter, the user separates the lid 164 from the lid holding ring 162 of the receiving container 160, which has been removed from the receiving housing 142, closes the upper end of the receiving container 160 with the lid 164, and discards the receiving container 160.

INDUSTRIAL APPLICABILITY

As described above, a safe lancet disposer 100 according to the present invention includes a cutting unit 110 which cuts an end of a needle (N) of a lancet (L), which is used for blood collection, a receiving unit 140 which is disposed under the cutting unit 110 to receive therein the cut end of the needle (N), and an operating unit 170 which is rotatably mounted to the receiving unit 140 and operates the cutting unit 110, so that the present invention prevents the lancet (L), having been used for blood collection, from being reused, thus preventing secondary infection and cross infection.

Furthermore, the present invention has a receiving container 160 which separately stores therein cut ends of needles (N), and a lid 164 which closes the receiving container 160. Consequently, the present invention is advantageous in that the receiving container 160 containing therein the needles (N) contaminated with blood can be safely sealed before being scrapped.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

The invention claimed is:

1. A safe lancet disposer, comprising:
a cutting unit, comprising: an insertion plate having therein an insertion hole into which an end of a needle of a lancet used for blood collection is inserted a support plate disposed under the insertion plate, with a guide groove formed in an upper surface of the support plate and extending from a first end of the support plate towards a second end, an elongated guide hole formed in the guide groove and communicating with the insertion hole, and a guide slot extending from the second end of the support plate to an intermediate position along the guide groove; and a cutting plate movably disposed in both the guide groove and the guide slot, with a cutting hole formed in the cutting plate and communicating with both the insertion hole and the elongated guide hole so as to cut the end of the needle inserted into the cutting hole through the insertion hole, a stop protrusion integrally provided under the cutting plate and extending towards the guide slot, and a mounting hole formed through the cutting plate;
a receiving unit, comprising: a receiving housing perpendicularly disposed under the support plate, with a receiving hole longitudinally formed through the receiving housing and communicating with the elongated guide hole; and a receiving container removably inserted into the receiving hole so that the cut end of the needle which drops through the elongated guide hole is contained in the receiving container; and
an operating unit, comprising: an operating lever rotatably mounted to a second surface of the receiving housing such that an upper end of the operating lever is coupled to the cutting plate through the guide slot, thus moving the cutting plate so as to cut the end of the needle inserted into the cutting hole,
wherein the receiving housing is coupled to the support plate and the insertion plate by a locking bolt, which is tightened to the receiving housing after passing through the support plate from an upper surface of the insertion plate, a lower surface of the receiving housing is defined by a stopper which openably closes the receiving hole, and the receiving housing comprises: a first hinge protrusion, provided on the second surface of the receiving housing at a position adjacent to an upper end of the receiving housing; a first spring seat, formed in the second surface of the receiving housing below the first hinge protrusion so that a first end of a lever spring is inserted into the first spring seat; and a first knurled surface, formed at a lower position on the second surface of the receiving housing.

2. A safe lancet disposer, comprising:

a cutting unit, comprising: an insertion plate having therein an insertion hole into which an end of a needle of a lancet used for blood collection is inserted; a support plate disposed under the insertion plate, with a guide groove formed in an upper surface of the support plate and extending from a first end of the support plate towards a second end, an elongated guide hole formed in the guide groove and communicating with the insertion hole, and a guide slot extending from the second end of the support plate to an intermediate position along the guide groove; and a cutting plate movably disposed in both the guide groove and the guide slot, with a cutting hole formed in the cutting plate and communicating with both the insertion hole and the elongated guide hole so as to cut the end of the needle inserted into the cutting hole through the insertion hole, a stop protrusion integrally provided under the cutting plate and extending towards the guide slot, and a mounting hole formed through the cutting plate;

a receiving unit, comprising: a receiving housing perpendicularly disposed under the support plate, with a receiving hole longitudinally formed through the receiving housing and communicating with the elongated guide hole; and a receiving container removably inserted into the receiving hole so that the cut end of the needle which drops through the elongated guide hole is contained in the receiving container; and an operating unit, comprising: an operating lever rotatably mounted to a second surface of the receiving housing such that an upper end of the operating lever is coupled to the cutting plate through the guide slot, thus moving the cutting plate so as to cut the end of the needle inserted into the cutting hole, wherein the operating lever comprises: a first lever body extending downwards from a position level with the upper end of the second surface of the receiving housing; a second lever body extending from a lower end of the first lever body outwards and downwards at a predetermined angle with respect to the second surface of the receiving housing; a third lever body extending downwards from a lower end of the second lever body; an operating protrusion provided on an upper surface of the first lever body and inserted into the mounting hole formed in the stop protrusion; second hinge protrusions provided on a first surface of the first lever body so that the second hinge protrusions are rotatably mounted to the first hinge protrusion via a hinge while being in close contact with opposite sides of the first hinge protrusion; a second spring seat formed in the first lever body below the second hinge protrusions so that a second end of the lever spring, which extends from the first spring seat to an outside, is inserted into the second spring scat; and a second knurled surface formed on a lower end of the third lever body at a position facing the first knurled surface.

3. The safe lancet disposer according claim 2, wherein the insertion plate comprises an insertion groove provided in an upper surface of the insertion plate so that an end of the lancet comes into close contact with a bottom of the insertion groove, the insertion halo is formed downwards in the insertion groove, and the guide slot divides the second end of the support plate into two opposite parts and defines a stop surface on an extension part of the guide groove so that the stop surface contacts a surface of the stop protrusion.

4. A safe lancet disposer, comprising:

a cutting unit, comprising: an insertion plate having therein an insertion hole into which an end of a needle of a lancet used for blood collection is inserted; a support plate disposed under the insertion plate, with a guide groove formed in an upper surface of the support plate and extending from a first end of the support plate towards a second end, an elongated guide hole formed in the guide groove and communicating with the insertion hole, and a guide slot extending from the second end of the support plate to an intermediate position along the guide groove; and a cutting plate movably disposed in both the guide groove and the guide slot, with a cutting hole formed in the cutting plate and communicating with both the insertion hole and the elongated guide hole so as to cut the end of the needle inserted into the cutting hole through the insertion hole, a stop protrusion integrally provided under the cutting plate and extending towards the guide slot, and a mounting hole formed through the cutting plate;

a receiving unit, comprising: a receiving housing perpendicularly disposed under the support plate, with a receiving hole longitudinally formed through the receiving housing and communicating with the elongated guide hole: and a receiving container removably inserted into the receiving hole so that the cut end of the needle which drops through the elongated guide hole is contained in the receiving container;

an operating unit, comprising: an operating lever rotatably mounted to a second surface of the receiving housing such that an upper end of the operating lever is coupled to the cutting plate through the guide slot, thus moving the cutting plate so as to cut the end of the needle inserted into the cutting hole; and an internal thread formed on a lower end of an inner surface of the receiving hole; and an external thread formed on a circumferential outer surface of a stopper, which operably closes the receiving hole so that the external thread corresponds to and engages with the internal thread.

5. A safe lancet disposer, comprising:

a cutting unit, comprising: an insertion plate having therein an insertion hole into which an end of a needle of a lancet used for blood collection is inserted; a support plate disposed under the insertion plate, with a guide groove formed in an upper surface of the support elate and extending from a first end of the support plate towards a second end, an elongated guide hole formed in the guide groove and communicating with the insertion hole, and a guide slot extending from the second end of the support plate to an intermediate position along the guide groove; and a cutting plate movably disposed in both the guide groove and the guide slot, with a cutting hole formed in the cutting plate and communicating with both the insertion hole and the elongated guide hole so as to cut the end of the needle inserted into the cutting hole through the insertion hole, a stop protrusion integrally provided under the cutting plate and extending towards the guide slot, and a mounting hole formed through the cutting plate;

a receiving unit, comprising: a receiving housing perpendicularly disposed under the support plate, with a receiving hole longitudinally formed through the receiving housing and communicating with the elongated guide hole; and a receiving container removably inserted into the receiving hole so that the cut end of the needle which drops through the elongated guide hole is contained in the receiving container; and an operating unit, comprising: an operating lever rotatably mounted to a second surface of the receiving housing such that an upper end of the operating lever is coupled to the cutting plate through the guide slot, thus moving the cutting plate so as to cut the end of the needle inserted into the cutting hole, wherein the receiving container has a cylindrical shape, which is open at an upper end thereof and closed at a lower end thereof, and the receiving container comprises: an integral lid holding ring extending downwards from the lower end of the receiving container; and a lid held by the lid holding ring so that, when the receiving container is full of cut ends of needles and is to be discarded, the opened upper end of the receiving container is closed using the lid.

6. The safe lancet disposer according to claim 5, further comprising: a magnet provided in the lower end of the receiving container so that the cut ends of the needles are held by the magnet in the receiving container.

7. The safe lancet disposer according to claim 5, wherein the insertion hole decreases in diameter from an upper end of the insertion groove towards a lower end of the insertion groove, and the cutting hole increases in diameter from a top of the guide groove towards a lower end of the support plate.

\* \* \* \* \*